(12) United States Patent
Gao et al.

(10) Patent No.: US 10,098,529 B2
(45) Date of Patent: Oct. 16, 2018

(54) OPTICAL DESIGN OF A LIGHT FIELD OTOSCOPE

(71) Applicants: Liang Gao, Santa Clara, CA (US); Ivana Tošić, Berkeley, CA (US); Noah Bedard, Pacifica, CA (US)

(72) Inventors: Liang Gao, Santa Clara, CA (US); Ivana Tošić, Berkeley, CA (US); Noah Bedard, Pacifica, CA (US)

(73) Assignee: Ricoh Company, LTD., Tokyo (JP)

( * ) Notice: Subject to any disclaimer, the term of this patent is extended or adjusted under 35 U.S.C. 154(b) by 74 days.

(21) Appl. No.: 15/197,601

(22) Filed: Jun. 29, 2016

(65) Prior Publication Data

US 2017/0119238 A1    May 4, 2017

Related U.S. Application Data

(63) Continuation-in-part of application No. 15/063,362, filed on Mar. 7, 2016.
(Continued)

(51) Int. Cl.
*A61B 1/227*    (2006.01)
*A61B 1/00*    (2006.01)
(Continued)

(52) U.S. Cl.
CPC .......... *A61B 1/227* (2013.01); *A61B 1/00163* (2013.01); *G02B 9/06* (2013.01); *G02B 9/12* (2013.01); *G02B 23/243* (2013.01); *G02B 23/2446* (2013.01); *G02B 27/0075* (2013.01); *H04N 5/2254* (2013.01); *G02B 13/0095* (2013.01); *H04N 2005/2255* (2013.01)

(58) Field of Classification Search
CPC .......................... A61B 1/227; A61B 1/00096
See application file for complete search history.

(56) References Cited

U.S. PATENT DOCUMENTS 4,664,486 A * 5/1987 Landre ............... G02B 23/2469
                                                  359/380
4,704,007 A * 11/1987 Landre ............... G02B 23/2469
                                                  359/380
(Continued)

FOREIGN PATENT DOCUMENTS

CN        1531410 A       9/2004
CN      101305899 A      11/2008
(Continued)

OTHER PUBLICATIONS

European Extended Search Report, European Application No. 16189044.7, dated Apr. 5, 2017, 8 pages.
(Continued)

*Primary Examiner* — Christian Sevilla
(74) *Attorney, Agent, or Firm* — Fenwick & West LLP

(57) ABSTRACT

Designs for a light field otoscope are disclosed. An example light field otoscope includes an objective lens group, relay optics and a plenoptic sensor (e.g., microlens array and sensor array). The objective lens group images an interior of a human ear and is characterized by a pupil plane and an image plane. The relay optics is positioned between the objective lens group and the plenoptic sensor. It relays the image plane to the microlens array and relays the pupil plane to the sensor array.

20 Claims, 10 Drawing Sheets

Related U.S. Application Data

(60) Provisional application No. 62/247,343, filed on Oct. 28, 2015.

(51) Int. Cl.
| | |
|---|---|
| *H04N 5/225* | (2006.01) |
| *G02B 27/10* | (2006.01) |
| *G02B 13/00* | (2006.01) |
| *G02B 27/00* | (2006.01) |
| *G02B 9/06* | (2006.01) |
| *G02B 9/12* | (2006.01) |
| *G02B 23/24* | (2006.01) |

(56) References Cited

U.S. PATENT DOCUMENTS

| | | | |
|---|---|---|---|
| 4,969,708 A * | 11/1990 | Leiner | A61B 1/00165 385/117 |
| 5,632,718 A * | 5/1997 | Igarashi | A61B 1/002 359/434 |
| 5,633,754 A * | 5/1997 | Hoogland | G02B 13/0095 359/434 |
| 5,919,130 A * | 7/1999 | Monroe | A61B 1/227 600/129 |
| 5,999,327 A | 12/1999 | Nagaoka | |
| 6,110,106 A | 8/2000 | MacKinnon et al. | |
| 6,142,934 A * | 11/2000 | Lagerway | A61B 1/00041 600/156 |
| 6,483,535 B1 | 11/2002 | Tamburrino et al. | |
| 7,058,441 B2 | 6/2006 | Shahar et al. | |
| 7,399,275 B2 | 7/2008 | Goldfain et al. | |
| 7,399,375 B2 | 7/2008 | Leiser et al. | |
| 7,433,042 B1 | 10/2008 | Cavanaugh et al. | |
| 7,448,753 B1 | 11/2008 | Chinnock | |
| 7,544,163 B2 | 6/2009 | MacKinnon et al. | |
| 7,723,662 B2 | 5/2010 | Levoy et al. | |
| 7,821,720 B2 * | 10/2010 | Wang | G02B 23/243 359/656 |
| 7,901,351 B2 | 3/2011 | Prescott | |
| 7,936,392 B2 | 5/2011 | Ng et al. | |
| 7,995,214 B2 | 8/2011 | Forster et al. | |
| 8,066,634 B2 | 11/2011 | Andreassen et al. | |
| 8,100,826 B2 | 1/2012 | MacKinnon et al. | |
| 8,107,086 B2 | 1/2012 | Hart et al. | |
| 8,143,565 B2 | 3/2012 | Berkner et al. | |
| 8,617,061 B2 | 12/2013 | Magalhaes Mendes et al. | |
| 8,824,779 B1 | 9/2014 | Smyth | |
| 8,944,596 B2 | 2/2015 | Wood et al. | |
| 8,949,078 B2 | 2/2015 | Berkner et al. | |
| 9,392,933 B2 | 7/2016 | Bedard | |
| 9,565,993 B2 | 2/2017 | Berkner et al. | |
| 9,706,116 B2 * | 7/2017 | Meng | H04N 5/23232 |
| 9,797,716 B2 * | 10/2017 | Meng | G01B 11/25 |
| 9,798,131 B2 * | 10/2017 | Shechterman | G02B 23/2415 |
| 2004/0147810 A1 | 7/2004 | Mizuno | |
| 2005/0010084 A1 * | 1/2005 | Tsai | A61B 1/00052 600/200 |
| 2005/0228231 A1 | 10/2005 | MacKinnon et al. | |
| 2005/0283065 A1 | 12/2005 | Babayoff | |
| 2007/0211605 A1 * | 9/2007 | Sakamoto | G02B 9/12 369/112.24 |
| 2008/0064925 A1 * | 3/2008 | Gill | A61B 1/00059 600/109 |
| 2008/0259274 A1 | 10/2008 | Chinnock | |
| 2009/0292168 A1 | 11/2009 | Farr | |
| 2010/0004513 A1 | 1/2010 | MacKinnon et al. | |
| 2010/0079741 A1 * | 4/2010 | Kraehmer | G03F 7/70308 355/71 |
| 2011/0026037 A1 | 2/2011 | Forster et al. | |
| 2011/0152621 A1 | 6/2011 | Magalhaes Mendes et al. | |
| 2012/0065473 A1 | 3/2012 | Andreassen et al. | |
| 2012/0182438 A1 | 7/2012 | Berkner et al. | |
| 2012/0226480 A1 | 9/2012 | Berkner et al. | |
| 2012/0320340 A1 | 12/2012 | Coleman, III | |
| 2012/0327426 A1 | 12/2012 | Hart et al. | |
| 2012/0327427 A1 | 12/2012 | Hart et al. | |
| 2013/0002426 A1 | 1/2013 | Hart et al. | |
| 2013/0002824 A1 | 1/2013 | Hart et al. | |
| 2013/0003078 A1 | 1/2013 | Hart et al. | |
| 2013/0027516 A1 | 1/2013 | Hart et al. | |
| 2013/0128223 A1 | 5/2013 | Wood et al. | |
| 2013/0237754 A1 | 9/2013 | Berglund et al. | |
| 2013/0289353 A1 | 10/2013 | Seth et al. | |
| 2014/0012141 A1 | 1/2014 | Kim et al. | |
| 2014/0192255 A1 | 7/2014 | Shroff et al. | |
| 2014/0206979 A1 * | 7/2014 | Berkner | A61B 1/227 600/407 |
| 2014/0316238 A1 * | 10/2014 | Berkner | G02B 23/243 600/407 |
| 2014/0350379 A1 | 11/2014 | Verdooner | |
| 2015/0005640 A1 | 1/2015 | Davis et al. | |
| 2015/0005644 A1 | 1/2015 | Rhoads | |
| 2015/0092071 A1 * | 4/2015 | Meng | H04N 5/2254 348/218.1 |
| 2015/0116526 A1 * | 4/2015 | Meng | G06T 5/50 348/218.1 |
| 2015/0117756 A1 | 4/2015 | Tosic et al. | |
| 2015/0126810 A1 | 5/2015 | Wood et al. | |
| 2015/0223669 A1 * | 8/2015 | Goldfain | A61B 3/12 600/109 |
| 2015/0238071 A1 * | 8/2015 | Hua | A61B 1/07 600/109 |
| 2015/0250381 A1 * | 9/2015 | Bedard | A61B 1/227 600/200 |
| 2017/0105615 A1 * | 4/2017 | Gao | A61B 3/0025 |
| 2017/0119238 A1 * | 5/2017 | Gao | A61B 1/227 |
| 2017/0127928 A1 * | 5/2017 | Berkner | A61B 1/227 |

FOREIGN PATENT DOCUMENTS

| | | |
|---|---|---|
| CN | 102105780 A | 6/2011 |
| CN | 102265124 A | 11/2011 |
| JP | H03-145614 A | 6/1991 |
| JP | 2000-126116 A | 5/2000 |
| JP | 2001-157664 A | 6/2001 |
| JP | 2002-34916 A | 2/2002 |
| JP | 2002-034916 A | 2/2002 |
| JP | 2007-004471 A | 1/2007 |
| JP | 2007-500541 A | 1/2007 |
| JP | 2009-244429 A | 10/2009 |
| JP | 2014-138858 A | 7/2014 |
| JP | 2014-530697 A | 11/2014 |
| WO | WO 2012/058641 A2 | 5/2012 |
| WO | WO 2012/066741 A1 | 5/2012 |
| WO | WO 2013/138081 A1 | 9/2013 |
| WO | WO 2014/021994 A1 | 2/2014 |

OTHER PUBLICATIONS

Bedard, N. et al., "Light Field Otoscope," Imaging and Applied Optics 2014, OSA Technical Digest (online), Optical Society of America, 2014, Paper IM3C.6, 4 pages.

Bedard, N. et al., "In Vivo Middle Ear Imaging with a Light Field Otoscope," Optics in the Life Sciences, OSA Technical Digest, (online), Optical Society of America, Paper BW3A.3, 2015, 3 pages.

Berkner, K. et al., "Measuring Color and Shape Characteristics of Objects from Light Fields," Imaging and Applied Optics, 2015, 3 pages.

Cho, N.H. et al., "Optical Coherence Tomography for the Diagnosis of Human Otitis Media," Proc. SPIE, 2013, 5 pages, vol. 8879, 88790N.

Hernandez-Montes, M.S. et al., "Optoelectronic Holographic Otoscope for Measurement of Nanodisplacements in Tympanic Membranes," Journal of Biomedical Optics, Proceedins of the XIth International Congress and Exposition, Society for Experimental Mechanics Inc., Jun. 2-5, 2008, 7 pages, vol. 14, No. 3.

Kim, C. et al., "Scene Reconstruction from High Spatio-Angular Resolution Light Fields," Transactions on Graphics (TOG), 2013, 11 pages, vol. 32, No. 4.

(56) References Cited

OTHER PUBLICATIONS

Kubota A. et al.,"View Interpolation using Defocused Multi-View Images," Proceedings of APSIPA Annual Summit and Conference, Asia-Pacific Signal and Information Processing Association, 2009 Annual Summit and Conference, Saporo, Japan, Oct. 4, 2009, pp. 358-362.

Kuruvilla, A. et al., "Otitis Media Vocabulary and Grammar," CMU, ICIP, 2012, 4 pages.

Levoy, M. "Light Field and Computational Imaging," IEEE Computer Magazine, 2006, pp. 46-55, vol. 39.

Levoy, M. et al., "Light Field Microscopy," Proc. SIGGRAPH, ACM Transactions on Graphics, 2006, pp. 1-11, vol. 25, No. 3.

Ng, R. et al., "Light Field Photography with a Hand-Held Plenoptic Camera," Stanford Tech Report, 2005, pp. 1-11.

Sundberg, M., et al., "Fibre Optic Array for Curvature Assessment—Application in Otitis Media," Medical & Biological Engineering & Computing, Mar. 2004, pp. 245-252, vol. 42, No. 2.

Sundberg, M., et al., "Diffuse Reflectance Spectroscopy of the Human Tympanic Membrane in Otitis Media," Physiological Measurement, 2004, pp. 1473-1493, vol. 25, No. 6.

Tao, M. et al., "Depth from Combining Defocus and Correspondence Using Light-Field Cameras," in Proceedings of the International Conference on Computer Vision, 2013, 8 pages.

Wanner, S. et al., "Globally Consistent Depth Labeling of 4D Light Fields," in Proceedings of the IEEE Computer Society Conference on Computer Vision and Pattern Recognition, 2012, pp. 41-48.

Yang, T. et al., "High Performance Imaging Through Occlusion via Energy Minimization-Based Optimal Camera Selection," International Journal of Advanced Robotic Systems, 2013, pp. 19, vol. 10.

U.S. Appl. No. 14/312,586, Lingfei Meng et al., filed Jun. 23, 2014.

U.S. Appl. No. 13/896,924, filed Jul. 8, 2015, 15 pages.

U.S. Appl. No. 61/946,267, filed Feb. 28, 2014.

U.S. Appl. No. 61/754,327, filed Jan. 18, 2013.

Chinese Office Action, Chinese Application No. 201410010071.X, dated May 6, 2015, 7 pages (with concise explanation of relevance).

U.S. Appl. No. 14/318,578, filed Dec. 10, 2015, 13 pages.

U.S. Appl. No. 14/318,578, filed Sep. 28, 2016, 11 pages.

Japanese Office Action, Japanese Application No. 2016-211050, dated Sep. 26, 2017, 5 pages (with concise explanation of relevance).

Japanese Office Action, Japanese Application No. 2014-006668, dated Sep. 26, 2017, 4 pages (with concise explanation of relevance).

\* cited by examiner

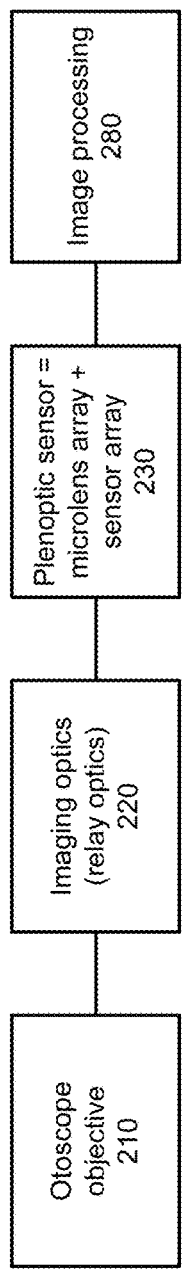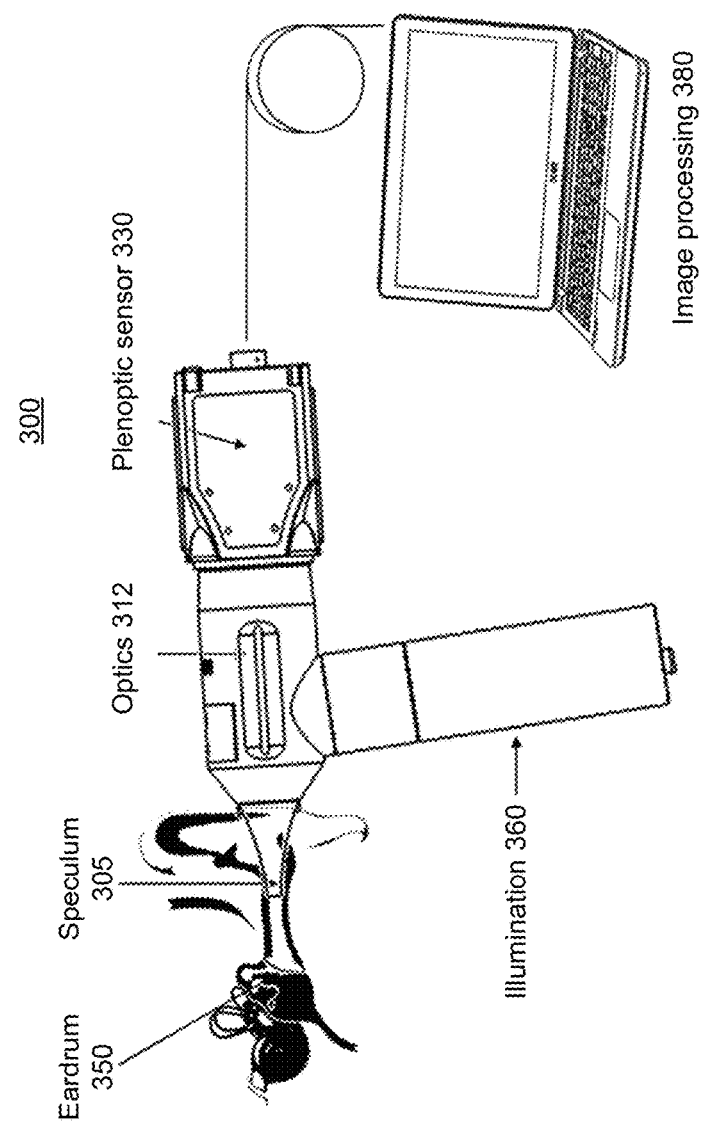
FIG. 2
FIG. 3

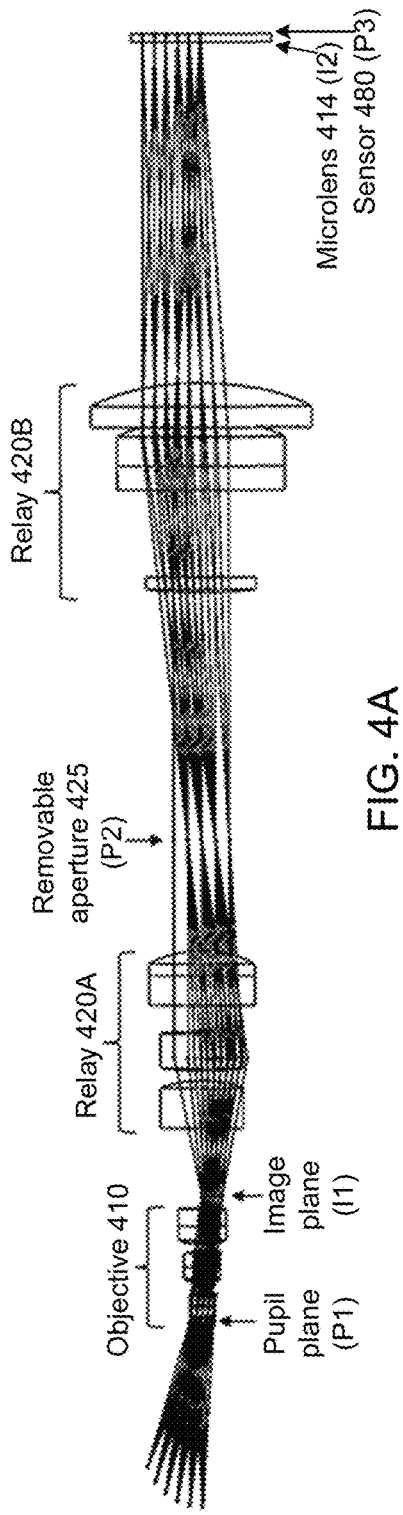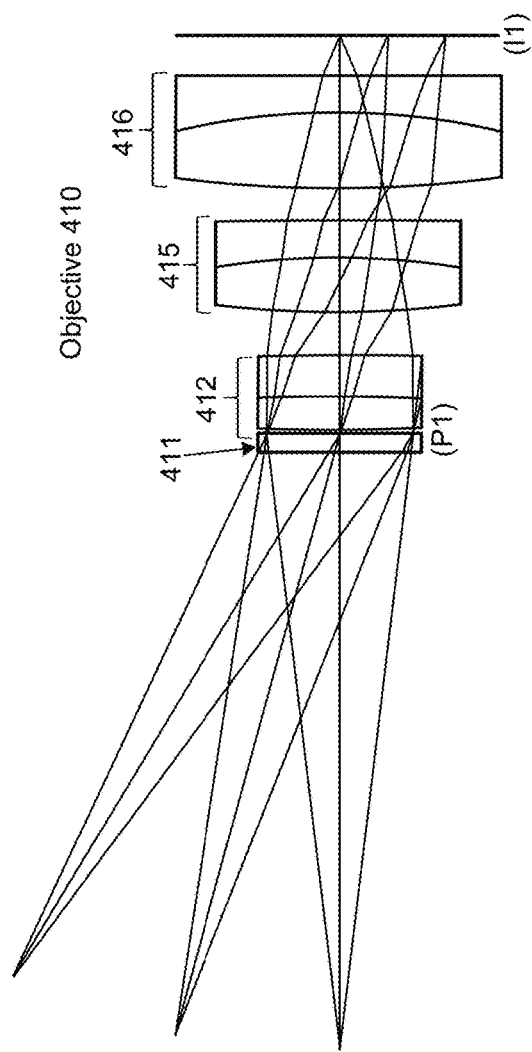
FIG. 4A
FIG. 4B

OPTICAL DESIGN OF A LIGHT FIELD OTOSCOPE

CROSS-REFERENCE TO RELATED APPLICATION(S)

This application is a continuation-in-part of U.S. patent application Ser. No. 15/063,362, "Optical Design of a Light Field Otoscope," filed Mar. 7, 2016; which claims priority under 35 U.S.C. § 119(e) to U.S. Provisional Patent Application Ser. No. 62/247,343, "Optical Design of a Light Field Otoscope," filed Oct. 28, 2015. The subject matter of all of the foregoing is incorporated herein by reference in their entirety.

BACKGROUND

1. Field of the Invention

This disclosure relates generally to light field otoscopes.

2. Description of Related Art

An otoscope is an optical imaging device used to view and diagnose disease in the middle ear. Clinicians use image features such as color, translucency, and three-dimensional (3D) shape of the tympanic membrane (TM) for diagnosis. Traditional otoscopes severely limit the field-of-view (FOV) and magnification of the TM. This creates monocular tunnel vision for the user, which reduces the ability to assess slight differences in shape and color. New digital otoscopes can provide high-resolution large FOV images, but their current imaging sensors do not provide quantitative measurements of 3D shape or color.

Compared to a traditional imaging sensor, a light field imaging sensor uses a microlens array to record the complete four-dimensional (4D) ray space. Light field data can be used to reconstruct multiple views of a scene, with each view having different perspective. These views can then be further post-processed to reconstruct 3D shape. However, the accuracy of the 3D reconstruction is dependent on many parameters of the optical system, such as the numerical aperture (NA), magnification, pixel pitch, and microlens pitch. Optics used in current otoscopes and otoscopes have parameters that result in low-accuracy light field 3D reconstructions.

Light field imaging sensors can also enable a modality called "multispectral imaging." Spectral images can be encoded into reconstructed views by placing optical filters in the aperture plane. Current optics within otoscopes and otoscopes contain very small and/or inaccessible apertures, which makes insertion of spectral filters impractical.

Therefore, there is a need for a new type of optical system designed for 3D and spectral measurement in otoscopy.

SUMMARY

The present disclosure overcomes the limitations of the prior art by providing various optical designs for a light field otoscope. An example light field otoscope includes an objective lens group, relay optics and a plenoptic sensor (e.g., microlens array and sensor array). The objective lens group images an interior of a human ear and is characterized by a pupil plane and an image plane. The relay optics is positioned between the objective lens group and the plenoptic sensor. It relays the image plane to the microlens array and relays the pupil plane to the sensor array.

Other aspects include various designs for the objective lens group. In one design, the otoscope objective consists of three lens elements, with the pupil plane positioned on the object-side of the objective and the image plane positioned on the image-side of the objective. In another design, the objective consists of a negative lens group followed by a second positive lens group, with the pupil plane positioned between the two lens groups.

In another aspect, the relay optics includes two relay lens groups. The first relay lens group relays the pupil plane to an intermediate pupil plane, which is then relayed by the second relay lens group to the sensor array. The two relay lens groups together also relay the image plane to the microlens array. Optionally, a filter module may be inserted at the intermediate pupil plane, for example to implement spectral imaging.

Various designs preferably have larger object-space numerical aperture, a larger and accessible aperture plane, and possibly also larger magnification.

Other aspects include components, devices, systems, improvements, methods, processes, applications, computer readable mediums, and other technologies related to any of the above.

BRIEF DESCRIPTION OF THE DRAWINGS

Embodiments of the disclosure have other advantages and features which will be more readily apparent from the following detailed description and the appended claims, when taken in conjunction with the accompanying drawings, in which:

FIG. 2 illustrates a plenoptic digital otoscope system, according to an embodiment.

FIG. 3 illustrates use of a light field otoscope to image the eardrum of a patient, according to an embodiment.

FIGS. 4A-4B are ray traces illustrating an optical design for a light field otoscope, according to an embodiment.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Figure 1A:
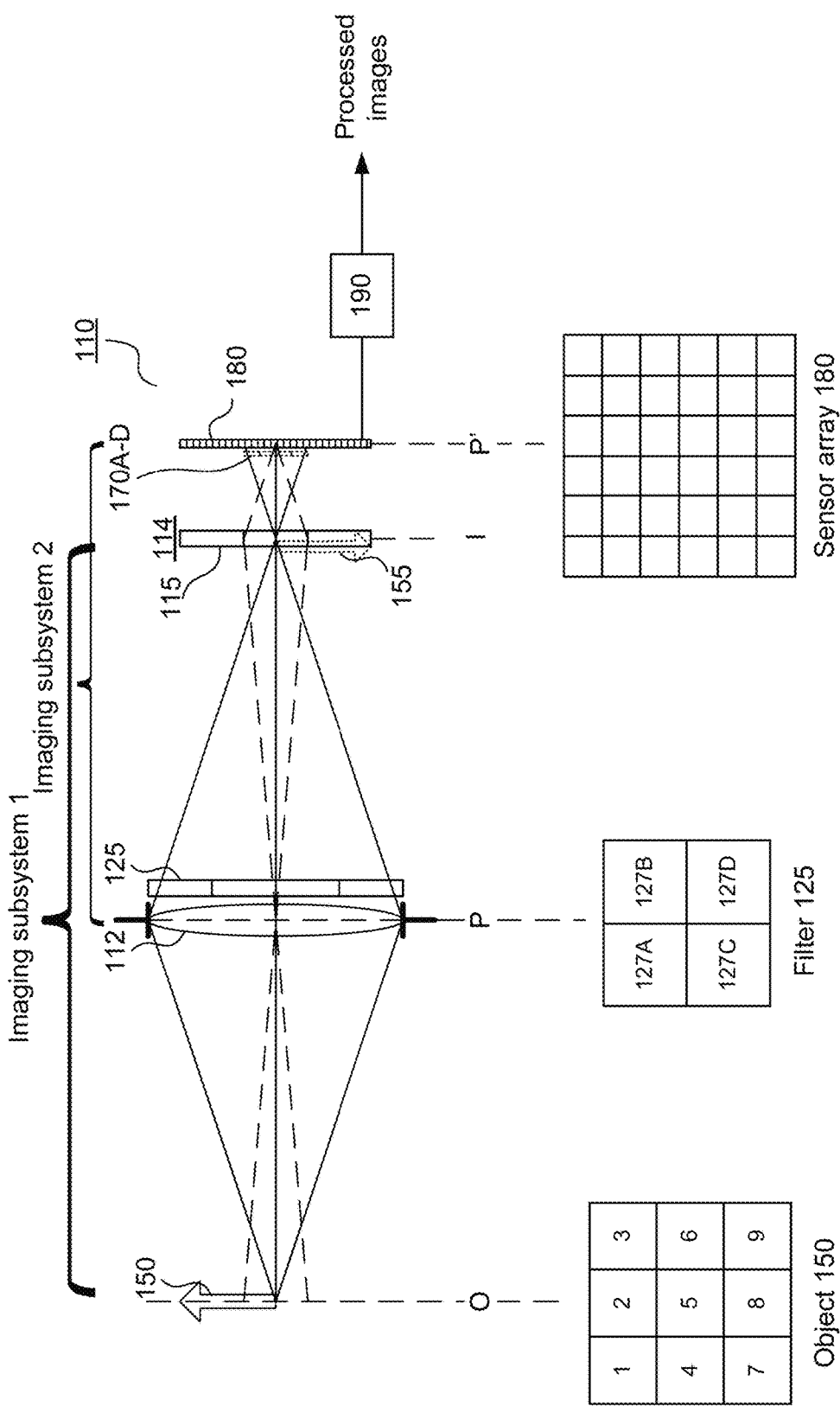
FIGS. 1A-1B (prior art) illustrates an example plenoptic imaging system.
Figure 1B:
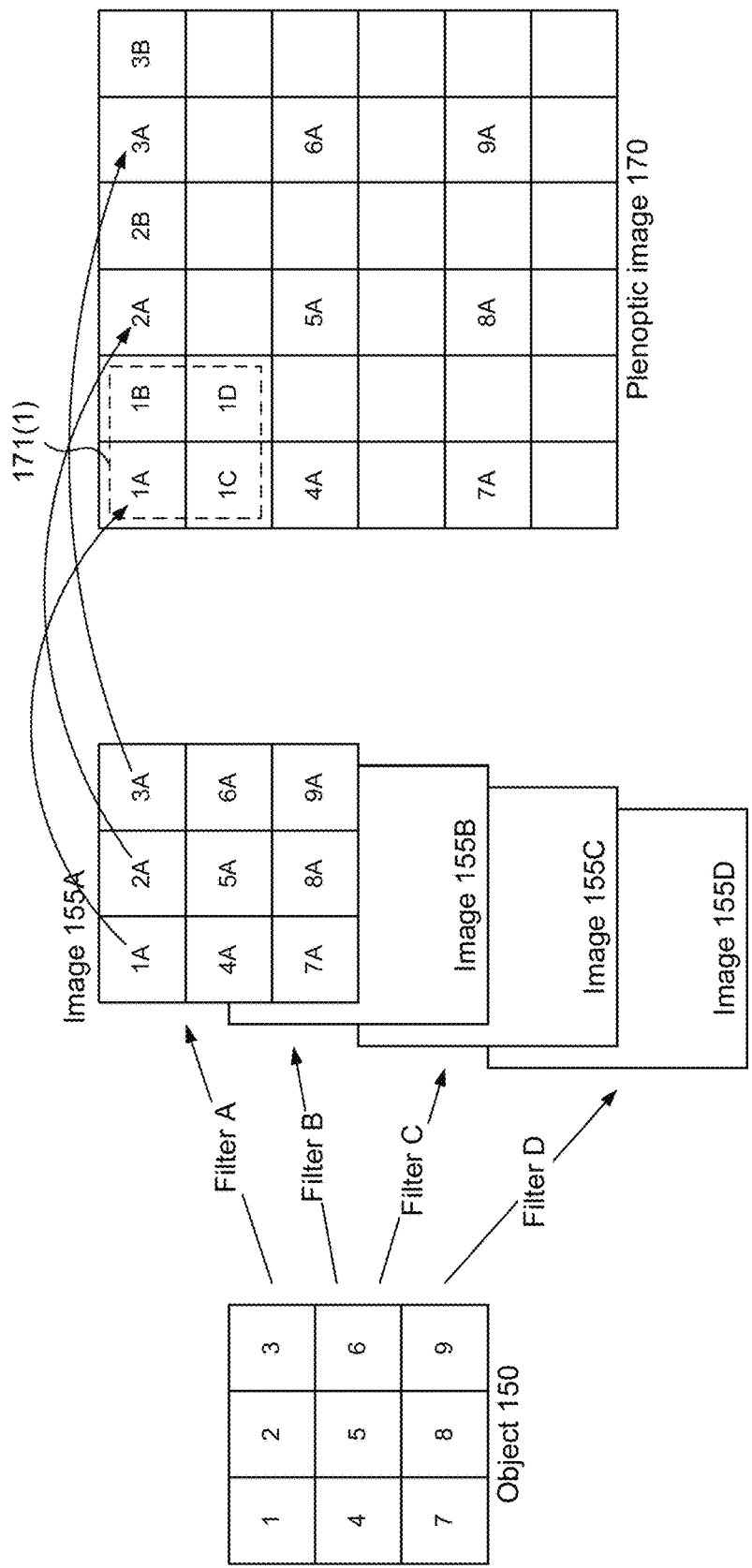

FIGS. 1A-1B (prior art) are diagrams illustrating an example light field or plenoptic imaging system. The plenoptic imaging system 110 includes a primary imaging subsystem 112 (represented by a single lens in FIG. 1A), a secondary imaging array 114 (an array of image forming elements 115) and a sensor array 180. The secondary imaging array 114 may be referred to as a microimaging array. These form two overlapping imaging subsystems, shown as imaging subsystem 1 and imaging subsystem 2 in FIG. 1A.

For convenience, the optical imaging group 112 is depicted in FIG. 1A as a single objective lens, but it should be understood that it could contain multiple elements. An object 150 is located at an object plane O. The objective lens 112 forms an optical image 155 of the object 150 at an image plane I. The microimaging array 114 is located at the image plane I. The system in its entirety forms spatially multiplexed and interleaved optical images 170 at the sensor array 180, which is located at a conjugate P' of the pupil plane P. For convenience, image 170 will be referred to as a plenoptic image. Examples of microimaging arrays 114 include microlens arrays, arrays of pinholes, micromirror arrays, checkerboard grids and waveguide/channel arrays. The microimaging array 114 can be a rectangular array, hexagonal array or other types of arrays. The sensor array 180 is also shown in FIG. 1A. For convenience, the locations of images, apertures and their optical conjugates will be referred to as planes (e.g., image plane, pupil plane), but it should be understood that the surface does not have to be perfectly planar.

Optionally, a filter module 125 is positioned at the pupil plane P (or one of its conjugates). The actual physical location may be before, after or in the middle of the optical imaging group 112. The filter module contains a number of spatially multiplexed filter cells 127A-D. In this example, the filter module 125 includes a rectangular array of filter cells 127, as shown in the bottom portion of FIG. 1A.

The bottom portion of FIG. 1A provides more detail. In this diagram, the object 150 is divided into a 3×3 array of regions, which are labeled 1-9. The filter module 125 is a 2×2 rectangular array of individual filter cells 127A-D. For example, each filter cell 127A-D may have a different spectral response. The sensor array 180 is shown as a 6×6 rectangular array.

FIG. 1B illustrates conceptually how the spatially multiplexed optical images 170A-D are produced and interleaved at sensor array 180. The object 150, if captured and filtered by filter cell 127A, would produce an optical image 155A. To distinguish optical image 155A from an unfiltered image of the object, the 3×3 regions are labeled with the suffix A: 1A-9A. Similarly, the object 150 filtered by filter cells 127B,C,D, would produce corresponding optical images 155B,C,D with 3×3 regions labeled 1B-9B, 1C-9C and 1D-9D. Each of these four optical images 155A-D is filtered by a different filter cell 127A-D within filter module 125 but they are all produced simultaneously by the plenoptic imaging system 110.

The four optical images 155A-D are formed in an interleaved fashion at the sensor plane, as shown in FIG. 1B. Using image 155A as an example, the 3×3 regions 1A-9A from optical image 155A are not contiguous in a 3×3 block within the plenoptic image 170. Rather, regions 1A, 1B, 1C and 1D, from the four different optical images, are arranged in a 2×2 fashion in the upper left of optical image 170 (the inversion of image 170 is neglected for clarity). Regions 2-9 are similarly arranged. Thus, the regions 1A-9A that make up optical image 170A are spread out across the plenoptic image 170, separated by portions of the other optical images 170B-D. Put in another way, if the sensor is a rectangular array of individual sensor elements, the overall array can be divided into rectangular subarrays 171(1)-(9) of sensor elements (only one subarray 171(1) is shown in FIG. 1B). For each region 1-9, all of the corresponding regions from each filtered image are imaged onto the subarray. For example, regions 1A, 1B, 1C and 1D are all imaged onto subarray 171(1). Note that since the filter module 125 and sensor assembly 180 are located in conjugate planes, each imaging element 115 in array 114 forms an image of the filter module 125 at the sensor plane P'. Since there are multiple imaging elements 115, multiple images 171 of the filter module 125 are formed.

The plenoptic image 170 can then be processed by processing module 190 to reconstruct desired images of the object. The processing could be deinterleaving and demultiplexing. It could also include more sophisticated image processing.

It should be noted that FIG. 1 has been simplified to illustrate underlying concepts. For example, the object 150 was artificially divided into an array in order to more easily explain the overall imaging function. The invention is not limited to arrayed objects. As another example, most practical systems will use significantly larger arrays, particularly at the sensor assembly and possibly also at the filter module. In addition, there need not be a 1:1 relationship between the 6×6 regions at the sensor plane and the underlying sensor elements in the sensor array. Each region could correspond to multiple sensor elements, for example. As a final example, the regions labeled 1 in the object, 1A in the filtered image 155A and 1A in the plenoptic image 170 do not have to be exact images of each other. In some designs, region 1A within plenoptic image 170 may capture the filtered energy approximately from region 1 in the object 150, but it may not actually be an image of region 1. Thus, the energy collected by sensor elements in region 1A of plenoptic image 170 may be integrating and sampling the image (or some transformation of the image) in region 1 in object 150, rather than representing a geometrical reproduction of the object at that region. In addition, effects such as parallax, vignetting, diffraction and optical propagation may affect any image formation.

The characteristics of a plenoptic imaging system can be used advantageously in otoscopes to image the interior of the ear. FIG. 2 is a block diagram of a plenoptic digital otoscope system. The system includes an otoscope objective 210, imaging optics (relay optics) 220, a plenoptic sensor 230 and image processing 280. The otoscope objective 210 can be an imaging objective, as used in conventional otoscopes. The imaging optics 220 works in conjunction with the otoscope objective 210 to form a conventional image within the otoscope instrument at an intermediate image plane. Rather than a conventional sensor array capturing this image, a plenoptic sensor 230 captures the image. The plenoptic sensor 230 is a sensor array with a microimaging array (e.g., a microlens array or pinhole array) mounted in front of it. The microimaging array is positioned at the intermediate image plane and a sensor array is positioned at a conjugate of the pupil plane. In addition, a filter module (not shown in FIG. 2) can be inserted at a pupil plane of the optical train (or at one of its conjugates) to allow spectral or other filtering of the light. The digital information extracted by the plenoptic sensor 230 is sent to a computing module 280 that performs the image processing of the plenoptic data. In this way, three-dimensional (3D) shapes, translucency and/or color information can be captured and extracted.

For example, the plenoptic otoscope may be operable in a depth imaging mode. In the depth imaging mode, the plenoptic image captured by the sensor array is processed to provide a three-dimensional depth image of an inside of an ear. Alternately or additionally, a plenoptic otoscope is operable in a spectral imaging mode. In the spectral imaging mode, plenoptic data captured by the sensor array is processed to provide two or more different spectral images of an inside of an ear. Disparity or depth maps can also be determined. The plenoptic otoscope may be switchable between the depth imaging mode and the spectral imaging mode or operate in both.

Another aspect relates to the use of the data captured by the plenoptic otoscope to assist in making a medical diagnosis. For example, the plenoptic data can be processed to produce enhanced imagery of the ear interior. Data based on the enhanced imagery can then be used to assist a person in making a medical diagnosis. This diagnostic data could be the enhanced imagery itself or it could involve further processing of the enhanced imagery.

Enhanced imagery of the tympanic membrane is a good example. A plenoptic otoscope can simultaneously capture depth and spectral information about the tympanic membrane. A depth map of the tympanic membrane can produce information regarding its shape—whether it is bulging or retracting, and the estimated curvature. Spectral information can include an amber or yellow image, which is especially useful to diagnose conditions of the tympanic membrane.

For example, Table 1 lists some features distinguishing the conditions of acute otitis media (AOM), otitis media with effusion (OME), and otitis media with no effusion. As can be seen from Table 1, the three conditions of the ear are different and they can be distinguished from one another based on one or more of the following features: color, position (e.g., 3D shape), and translucency. In order to make correct diagnosis of the ear condition, otoscopic images capturing accurate information about color, 3D shape and translucency of an inside of an ear (e.g., a tympanic membrane in an ear canal) are desirable. These can all be captured simultaneously by a plenoptic otoscope.

TABLE 1

| Otoscopic findings associated with clinical diagnostic categories on TM images | | | |
|---|---|---|---|
| | AOM | OME | NOE |
| Color | White, pale yellow, markedly red | White, amber, gray, blue | Gray, pink |
| Position | Distinctly full, bulging | Neutral, retracted | Neutral, retracted |
| Translucency | Opacified | Opacified, semi-opacified | Translucent |

Plenoptic data also includes multiple views of the same image. This allows the user to refocus to different depths in the image and to view the same image from different viewpoints. For example, the effect of occluding objects may be reduced by taking advantage of multiviews. This could be accomplished by refocusing. Alternately, it could be accomplished by segmenting the light field (multiple views) into depth layers.

FIG. 3 illustrates use of a plenoptic otoscope 300 to image the eardrum 350 of a patient. In this example, the otoscope 300 is handheld and includes a main body and a handle. The main body houses the optics 312 and the plenoptic sensor 330. The handle includes illumination 360 for the otoscope 300. Referring to FIG. 2, the optics 312 includes the otoscope objective 210 and the relay optics 220. A disposable speculum 305 is attachable to the tip of the otoscope. In this example, the output of the plenoptic sensor 330 is transmitted to a separate computer system 380, which processes the captured plenoptic images and displays the desired results.

General goals for the optical design of a light field otoscope typically include to maximize field of view (FOV), depth-of-field (DOF), depth accuracy, image resolution, and spectral resolution, while minimizing lens diameters, number of lenses, sensor size, and aberrations. Many of these goals are competing. For example, increasing DOF will decrease the depth accuracy; increasing image resolution requires either a larger sensor or reduced depth accuracy; and reducing lens diameter or number of lenses will typically worsen aberrations. Given these tradeoffs, the following describes some design choices for the light field otoscope.

Anatomical Constraints.

The light field otoscope images the tympanic membrane (TM), which has a diameter of 7-10 mm. In practice, a clinician should see some area around the TM to guide image acquisition, yielding a larger FOV of typically 10-20 mm diameter. A typical mechanical working distance from the front of an ear speculum to the TM is 15-25 mm. The tip of the ear speculum typically should be at most 3 mm diameter for imaging children and typically at most 5 mm for imaging adults; in both cases the speculum can be cone-shaped having an increasing diameter proximally, at an angle of approximately 8 degrees or less. These anatomical constraints affect the FOV, mechanical working distance, first lens diameter, and spacing/diameter of subsequent lenses.

Object-Space NA.

Depth accuracy is dependent on the object-space numerical aperture (NA), magnification, microlens size, pixel size, and performance of the post-processing algorithms. In a light field camera, the object-space NA of the main lens determines the degree of parallax between reconstructed multi-view images. Greater parallax provides more pixel disparity in multi-view images, which yields a more accurate depth map. Object-space NA of a thin lens is given by:

$$NA = n \sin \theta \approx nD/2f \quad (1)$$

where refractive index n=1 in air, D is the diameter of the lens, and f is the focal length of the lens. For imaging the middle ear, the maximum diameter of the first lens surface preferably should be less than the speculum diameter (e.g., 3 mm) to allow space for illumination optics. The object-space NA can be maximized by placing the stop at the first lens surface. The stop diameter can be equivalent to the first lens diameter, which yields the greatest object-space NA, but produces off-axis vignetting. Increasing object-space NA also causes decreased DOF, which can make it difficult to acquire in-focus images of the TM. In practice, object-space NA preferably should be selected to balance depth accuracy and a user-friendly DOF.

Magnification, Microlens Pitch, Pixel Pitch.

Magnification of the main lens determines the sensor size, as well as the image-space NA. A large magnification requires a larger sensor, larger proximal lenses, and typically a longer optical train, resulting in a more bulky device. However, a large magnification also produces a smaller image-space NA. In a light field camera, image-space NA of the main lens preferably should match the microlens NA. Also, the microlens NA determines the diffraction-limited spot size, which preferably should match approximately a two-pixel diameter on the sensor. Finally, the total number of microlenses determines the number of spatial samples in each multiview image, and the number of pixels behind each microlens determines the number of multiview images. Therefore, magnification, microlens pitch, and pixel pitch should be optimized for spatial resolution, depth accuracy, and overall system size.

Aberrations: Field Curvature and Distortion.

Aberrations in lens systems are typically corrected using additional lens elements, aspherical surfaces, and/or specialized optical materials. In contrast, a light field camera uses computational imaging to reconstruct images, so some aberrations such as lateral distortion and field curvature can be digitally corrected. Reducing tolerances of optical aberrations can simplify the final lens assembly, enabling a more compact overall design.

Synthetic Aperture.

In a light field camera, images can be reconstructed from different positions or diameters of the main lens aperture. For example, an image can be reconstructed from the full aperture, which results in the smallest DOF; or an image can be reconstructed from a portion of the aperture corresponding to one de-magnified pixel, which results in the largest DOF. In a light field otoscope, each multiview image corresponds to an image from through the aperture of one de-magnified pixel. When designing the main lens, aberrations can be analyzed for each (small aperture) multiview image instead of for the full aperture. In particular, vignetting for each multiview image has different performance than for the full aperture. An optimized design preferably considers aberrations for several aperture sizes and positions.

Example Optical Design 1

Figure 4C:
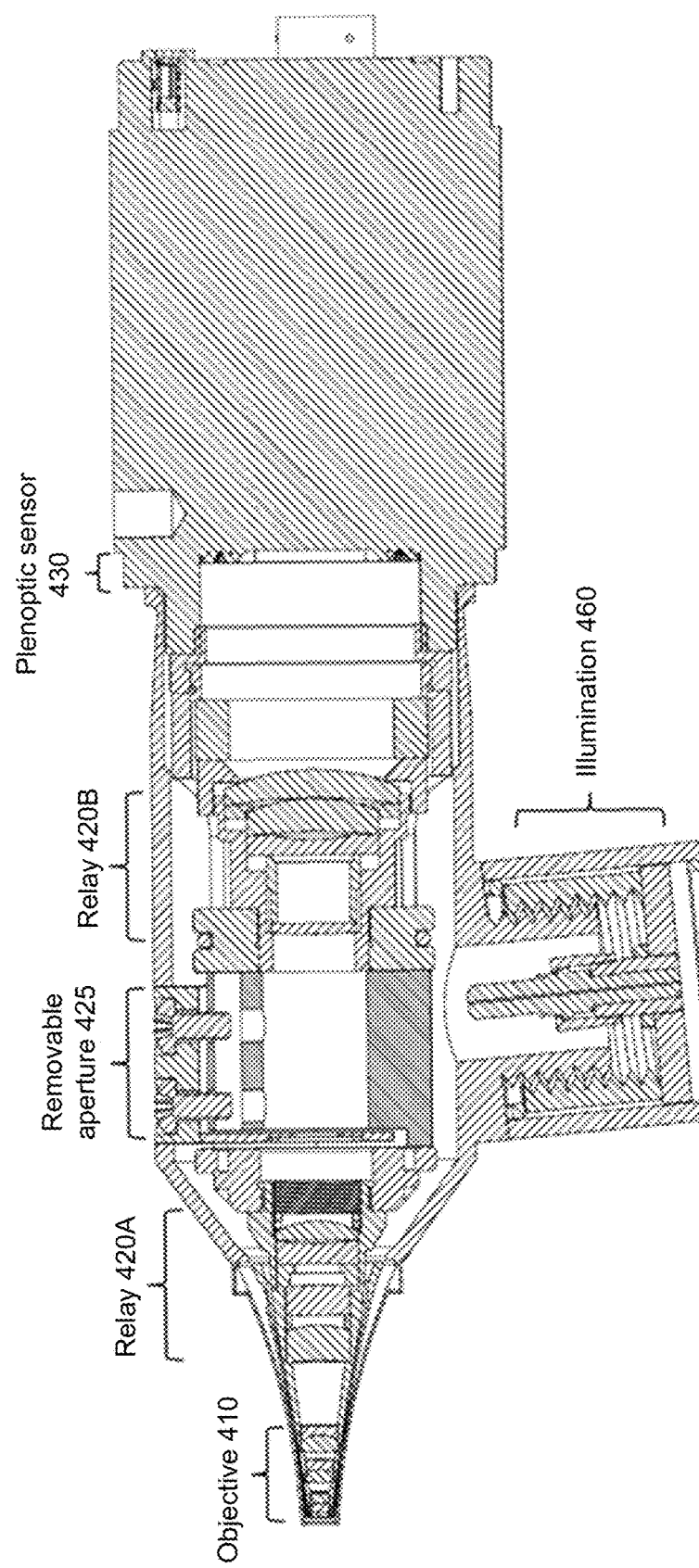
FIGS. 4C-4D are cross-sectional views illustrating an optomechanical design for the design of FIGS. 4A-4B.

FIGS. 4A-4D illustrate an example design for a light field otoscope. FIG. 4A shows the entire optical train. This design includes three lens groups: an objective lens group 410 and two relay lens groups 420A, 420B. FIG. 4B is a ray trace of the objective 410. The objective lens group 410 contains a pupil plane P1 towards the front of the objective lens group, so that object-space NA and FOV are maximized while reducing vignetting. In this example, the pupil plane P1 is near the front of the front lens of the objective lens group 410. An image is formed at the rear of the objective lens at image plane I1. Chief rays in the image-space are near telecentric, creating a distant exit pupil that is re-imaged by the following relay lens group 420A. A working distance of 15-25 mm is determined by anatomical constraints of the ear canal. The FOV of 10-20 mm at nominal working distance is selected to image the TM and surrounding ear canal. The overall size of the lens group is constrained by the diameter of the ear canal. In one embodiment, the objective lens group has three doublet lens elements 412, 415, 416 of focal length 9, 9, and 10 mm. The three lenses have increasing diameter of 2, 3, and 4 mm. The object-space NA is 0.06 and paraxial magnification is −0.3. The distal tip also contains a sapphire window 411 for protection of lens elements. The entire objective lens group is contained within the distal tip of the ear speculum.

The first relay lens group 420A is used to re-image and magnify the pupil. An aperture stop 425 (with removable aperture) is placed at the re-imaged pupil plane P2. The second relay lens group 420B forms an image of the object onto the microlens array at I2, which is a conjugate of image plane I1. The relay lens group 420B is positioned one focal length from the aperture stop location P2 and one focal length from the image plane I2, such that rays are image-space telecentric.

The focal lengths of the relay lenses are determined by desired magnification in the system. In a light field camera, the desired size of the object image matches the image sensor, while the desired size of the pupil image matches a microlens. In one approach, the f-number of the main lens (or image-space NA) should match the f-number of the microlens.

The size $D_{P2}$ of the aperture stop 425 located at pupil plane conjugate P2 is given by:

$$D_{P2} \approx D_{P1} * F_{Relay\_Lens1} / F_{Objective\_Lens} \qquad (2)$$

where $D_{P1}$ is the pupil diameter in the objective lens group and $F_{Relay\_Lens1}$ is the focal length of the first relay lens group 420A. Given anatomical constraints of the ear canal, $D_{P1}$ should be <=2 mm diameter. The size $D_{P3}$ of the pupil image formed by a microlens 414 on the image sensor 480 (at pupil plane conjugate P3) is given by:

$$D_{P3} \approx D_{P2} * F_{Microlens} / F_{Relay\_Lens2} \qquad (3)$$

where $F_{Microlens}$ is the focal length of a microlens 414 and $F_{Relay\_Lens2}$ is the focal length of the second relay lens group 420B.

The size $D_{I2}$ of the image relayed onto the microlens array 414 at image plane conjugate I2 is given by:

$$D_{I2} \approx FOV * M * F_{Relay\_Lens2} / F_{Relay\_Lens1} \qquad (4)$$

where FOV is the FOV of the objective lens group 410 and M is the magnification of the objective lens group.

In one embodiment of a light field otoscope, a 1-inch format image sensor containing 3.69 micron pixels with a 50 micron pitch microlens array is used. Therefore, f=12 mm was selected for the first relay lens 420A, f=35 mm was selected for the second relay lens 420B, and f=0.37 mm was selected for the microlens array 414 (corresponding to f-number=7.25). Table 2 below gives the lens prescription, where the two relay lens groups 420A, 420B are modelled as paraxial lenses.

TABLE 2

Lens Prescription

| Surf | Type | Radius | Thickness | Glass | Diameter | Comments |
|---|---|---|---|---|---|---|
| OBJ | STANDARD | Infinity | 16 | | 14 | |
| 1 | STANDARD | Infinity | 0.5 | SAPPHIRE | 2 | 411 |
| 2 | STANDARD | Infinity | 0 | | 2 | |
| 3 | STANDARD | 5.38 | 1 | S-PHM52 | 2 | 412 |
| 4 | STANDARD | −5.38 | 1 | N-LASF9 | 2 | 412 |
| 5 | STANDARD | −20.79 | 1.2 | | 2 | |
| 6 | STANDARD | 5.26 | 1.47 | N-BK7 | 3 | 415 |
| 7 | STANDARD | −3.98 | 1.03 | N-SF5 | 3 | 415 |

TABLE 2-continued

Lens Prescription

| Surf | Type | Radius | Thickness | Glass | Diameter | Comments |
|---|---|---|---|---|---|---|
| 8 | STANDARD | −12.05 | 0.8 | | 3 | |
| 9 | STANDARD | 7.12 | 2 | N-BAF10 | 4 | 416 |
| 10 | STANDARD | −4.22 | 1 | N-SF10 | 4 | 416 |
| 11 | STANDARD | −33.66 | 1.061952 | | 4 | |
| 12 | STANDARD | Infinity | 12 | | 4.104906 | (I1) |
| 13 | PARAXIAL | — | 19 | | 11.29943 | 420A Focal length = 12 |
| STO | STANDARD | Infinity | 35 | | 4.8 | (P2) |
| 15 | PARAXIAL | — | 35 | | 15.17749 | 420B Focal length = 35 |
| 16 | STANDARD | Infinity | 0 | | 12 | |
| 17 | USERSURF | 0.171 | 0.525 | 1.460000, 67.900000 | 12 | 414 |
| 18 | STANDARD | Infinity | 0.01 | | 12 | |
| IMA | STANDARD | Infinity | | | 12.05053 | 480 |

The first order lens parameters for this design are the following:

| | |
|---|---|
| Field of view (diameter) | 10 mm |
| NA at the object side | 0.0602 |
| NA at the image side | 0.0684 (matching the NA of the microlens) |
| Working distance | 16 mm |
| Paraxial magnification | 0.88 |

Figure 4D:
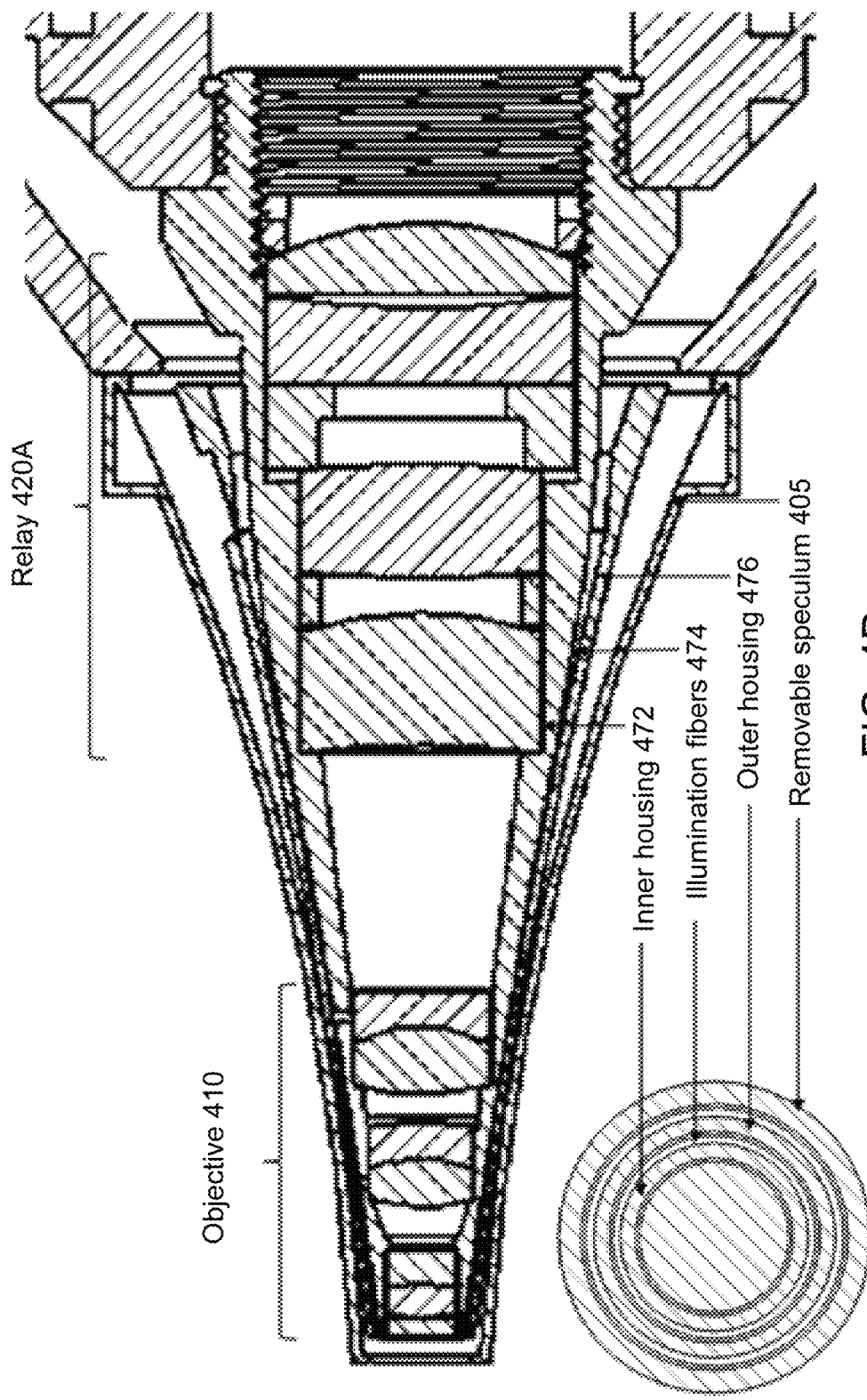

FIG. 4C-4D are cross-sectional views illustrating an opto-mechanical design for this light field otoscope. FIG. 4C shows the entire body, from objective 410 to plenoptic sensor 430. FIG. 4D is a magnification showing primarily the objective lens group 410. The objective lens group 410 is contained within the tip of a cone-shaped internal housing 472 with cavities to mount each lens element. Illumination fibers 474 are epoxied radially around the surface of the inner housing 472. A second cone-spaced outer housing 476 is placed over the illumination fibers 474 for protection. A removable speculum 405 can be placed over the outer housing 476.

The first relay lens group 420A is also placed within the inner housing 472. The inner housing mounts to a lens tube, which contains a removable aperture 425 and the second relay lens group 420B. A filter module can be placed at the removable aperture 425. The lens tube is mounted to a camera body with integrated microlens array. The lens tube is contained inside a protective housing and also connected to a handle. The handle contains an illumination source 460 coupled to illumination fibers, a battery, and electronics.

Example Optical Design 2

Figure 5A:
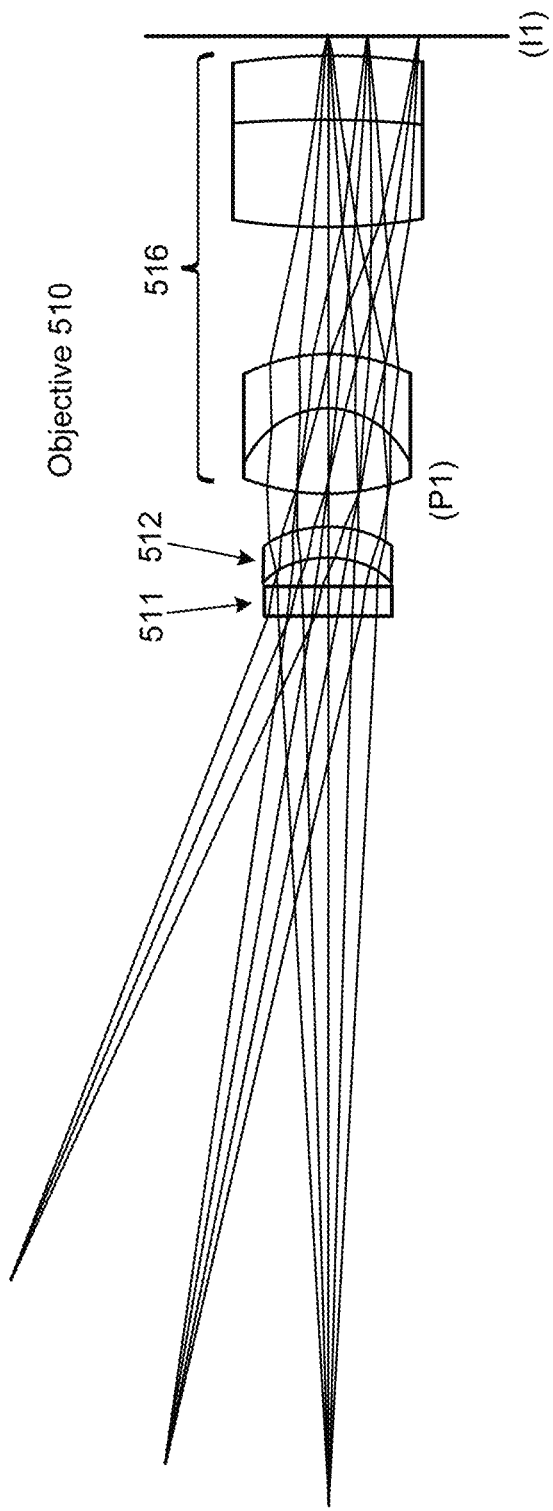
FIG. 5A is a ray trace illustrating an example optical design for an objective lens for a plenoptic otoscope, according to an embodiment.
Figure 5B:
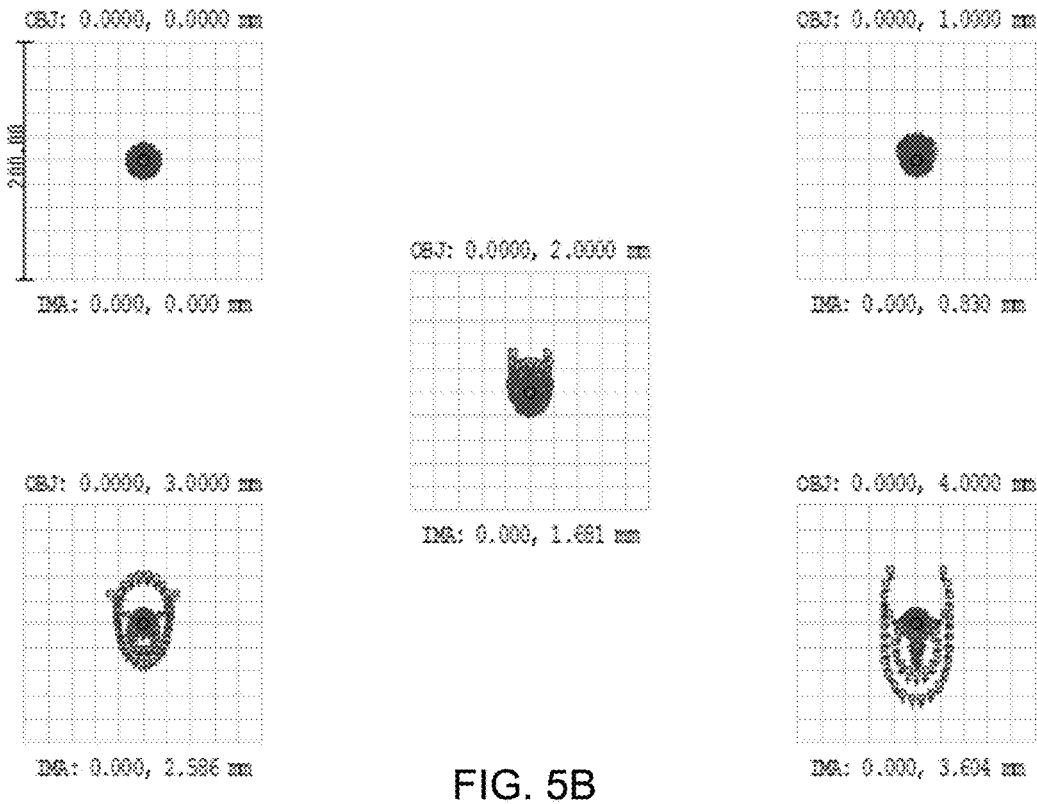
FIG. 5B are spot diagrams for the otoscope design based on FIG. 5A.

FIGS. 5A-5B illustrate another design for the objective lens group of a light field otoscope. The rest of the design is based on the same principles as shown in FIGS. 4A-4D. FIG. 5A is a ray trace through the objective lens group 510. This design consists of two lens groups, which are separated by a physical aperture. The first negative lens group 512 is a meniscus lens, which collimates the incident light rays into a pupil P1. The objective lens group 510 contains a pupil plane P1 towards the front of the objective lens group, so that object-space NA and FOV are maximized while reducing vignetting. In this example, the pupil plane P1 is near the back of the front lens of the objective lens group 510. The second positive lens group 516 consists of two achromatic doublets, which bend light rays and form an image at an intermediate plane I1. As in the design of FIG. 4, the resultant intermediate image is then relayed to the plenoptic sensor by two relay lens groups, which are not shown in FIG. 5. The optical prescription for the entire optical train is shown in Table 3. The two relay lens groups are modeled as paraxial optics. The design also includes a sapphire window 511.

TABLE 3

Lens Prescription

| Surf | Type | Radius | Thickness | Glass | Diameter | Comment |
|---|---|---|---|---|---|---|
| OBJ | STANDARD | 5.3 | 14 | | 10 | |
| 1 | STANDARD | Infinity | 0.5 | SAPPHIRE | 2 | 511 |
| 2 | STANDARD | Infinity | 0.44 | | 2 | |
| 3 | STANDARD | −1.51 | 0.5 | N-BK7 | 2 | 512 |
| 4 | STANDARD | −1.66 | 0.5 | | 2 | |
| 5 | STANDARD | Infinity | 0 | | 2 | (P1) |
| 6 | STANDARD | 3.45 | 1.37 | N-BK7 | 2.6 | 516 |
| 7 | STANDARD | −1.38 | 0.83 | N-SF5 | 2.6 | 516 |
| 8 | STANDARD | −2.87 | 2 | | 2.6 | |
| 9 | STANDARD | 10.14 | 1.68 | N-BK7 | 3 | 516 |
| 10 | STANDARD | −16.85 | 1 | N-SF5 | 3 | 516 |
| 11 | STANDARD | −10.65 | 0.7 | | 3 | |
| 12 | STANDARD | Infinity | 13.5 | | 6 | (I1) |
| 13 | PARAXIAL | — | 23 | | 13.0 | Focal length = 12 |

TABLE 3-continued

Lens Prescription

| Surf | Type | Radius | Thickness | Glass | Diameter | Comment |
|---|---|---|---|---|---|---|
| STO | STANDARD | Infinity | 35 | | 4.8 | (P2) |
| 15 | PARAXIAL | — | 15.67 | | 11.85 | 420B Focal length = 35 |
| 16 | STANDARD | Infinity | 0 | | 12 | |
| 17 | USERSURF | 0.171 | 0.525 | 1.460000, 67.900000 | 12 | 414 |
| 18 | STANDARD | Infinity | 0.01 | | 12 | |
| IMA | STANDARD | Infinity | | | 11.04 | 480 |

The first order lens parameters for this design are the following:

| | |
|---|---|
| Field of view (diameter) | 10 mm |
| NA at the object side | 0.0566 |
| NA at the image side | 0.0684 (matching the NA of the microlens) |
| Working distance | 14 mm |
| Paraxial magnification | 0.83 |

FIG. 5B shows spot diagrams for this design (excluding the microlens array).

Figure 5C:
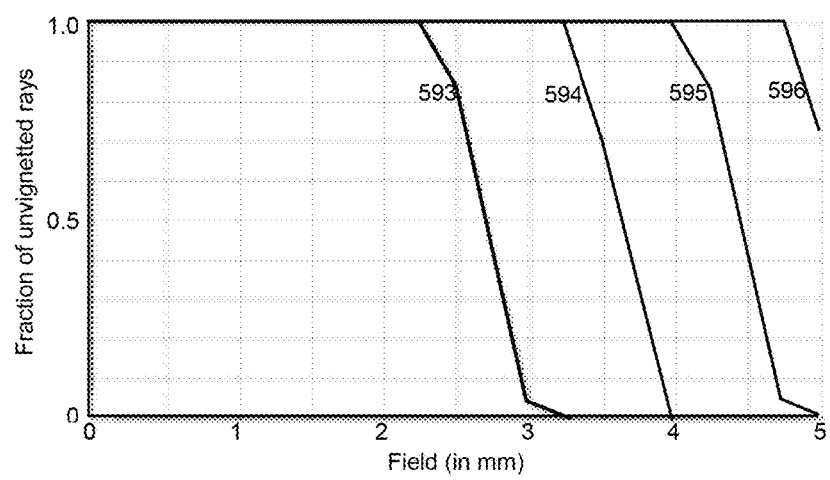
FIG. 5C is a graph showing vignetting for the light field otoscope of FIGS. 5A-5B.

FIG. 5C is a graph showing vignetting of this design for different object distances. Each curve plots the fraction of unvignetted rays passing through a pinhole aperture (0.1 mm radius) at the edge of the pupil (y=2.4 mm). Each curve corresponds to a different object location. The leftmost curve 593 (most vignetting) corresponds to an object that is 6 mm closer to the plenoptic otoscope than the nominal focus position. From left to right, curve 594 corresponds to 3 mm closer than nominal focus, curve 595 is at the nominal focus, and curve 596 corresponds to 3 mm farther than nominal focus. For an object that is 6 mm farther than nominal focus, there is no vignetting across the field shown. This design has good vignetting characteristics.

Example Optical Design 3

Figure 6A:
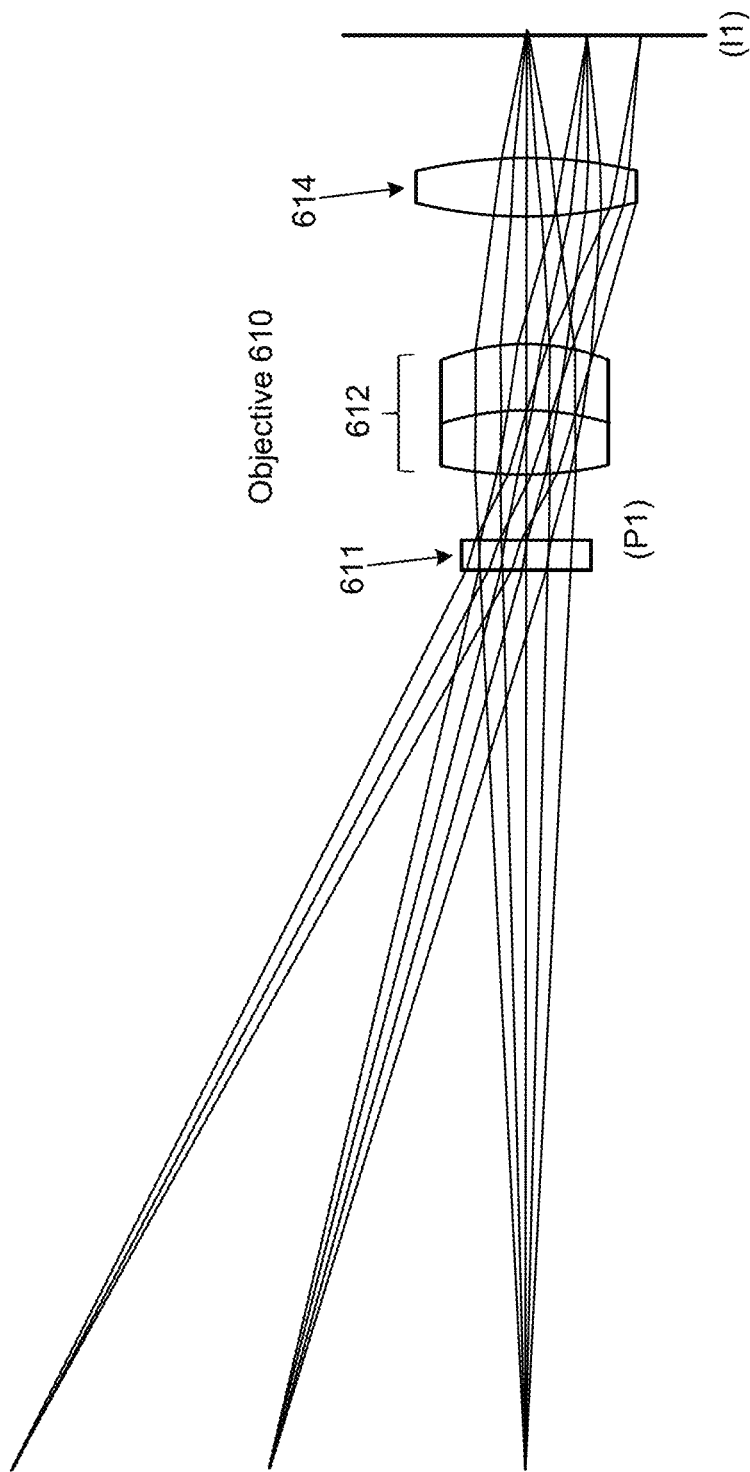
FIG. 6A is a ray trace illustrating another example optical design for an objective lens for a plenoptic otoscope, according to an embodiment.

FIG. 6A illustrates another design for the objective lens group of a light field otoscope. The rest of the design is based on the same principles as shown in FIGS. 4A-4D. FIG. 6A is a ray trace through the objective lens group 610. The objective 610 includes a sapphire window 611, a doublet 612, and a singlet 614. The entrance pupil (P1) is located at the back surface of the sapphire window 611, maximizing the optical throughput. As in the design of FIG. 4, the resultant intermediate image is then relayed to the plenoptic sensor by two relay lens groups, which are not shown in FIG. 6. The optical prescription for the entire optical train is shown in Table 4. The two relay lens groups are modeled as paraxial optics.

TABLE 4

Lens Prescription

| Surf | Type | Radius | Thickness | Glass | Diameter | Comment |
|---|---|---|---|---|---|---|
| OBJ | STANDARD | Infinity | 14 | | 16 | |
| 1 | STANDARD | Infinity | 0.5 | SAPPHIRE | 2 | 611 |
| 2 | STANDARD | Infinity | 0 | | 2 | |
| 3 | STANDARD | Infinity | 1 | | 2 | (P1) |
| 4 | STANDARD | Infinity | 0 | | 2 | |
| 5 | STANDARD | 5.33 | 1.00 | N-BK7 | 2.6 | Conic-17.08 Element 612 |
| 6 | STANDARD | -4 | 1 | N-SF5 | 2.6 | 612 |
| 7 | STANDARD | -3.7 | 2 | | 2.6 | |
| 8 | STANDARD | 7 | 0.92 | N-BK7 | 3.4 | 614 |
| 9 | STANDARD | -7 | 2.2 | | 3.4 | |
| 10 | STANDARD | Infinity | 12 | | 6 | (I1) |
| 11 | PARAXIAL | — | 12 | | 8.66 | 420A |
| 12 | COORDBRK | — | 0 | | — | Element Tilt |
| STO | STANDARD | Infinity | 0 | | 4.8 | (P2) |
| 14 | COORDBRK | — | 35 | | — | Element Tilt |
| 15 | PARAXIAL | — | 33.0 | | 14.26 | 420B |
| 16 | USERSURF | 0.171 | 0.525 | 1.46, 67.9 | 12 | 414 |
| 17 | STANDARD | Infinity | 0.01 | | 12 | |
| IMA | STANDARD | Infinity | | | 11.05 | 480 |

The first order lens parameters for this design are the following:

| | |
|---|---|
| Field of view (diameter) | 16 mm |
| NA at the object side | 0.051 |
| NA at the image side | 0.0684 (matching the NA of the microlens) |
| Working distance | 14 mm |
| Paraxial magnification | 0.74 |

We calculated the RMS (root mean square) of spot diagrams at the micro-lens array (MLA) for different field heights in Zemax and show the results in Table 5. Since the design is optimized for on-axis objects, the RMS spot size is smallest on-axis. For on-axis objects, the resolution is diffraction limited.

TABLE 5

RMS Spot Size

| Field height (mm) | RMS spot (um) |
|---|---|
| 0 | 5.1 |
| 1 | 6.7 |
| 2 | 9.9 |
| 3 | 13.7 |
| 4 | 17.8 |
| 5 | 22.0 |
| 6 | 26.7 |
| 7 | 32.2 |
| 8 | 47.8 |

Figure 6B:
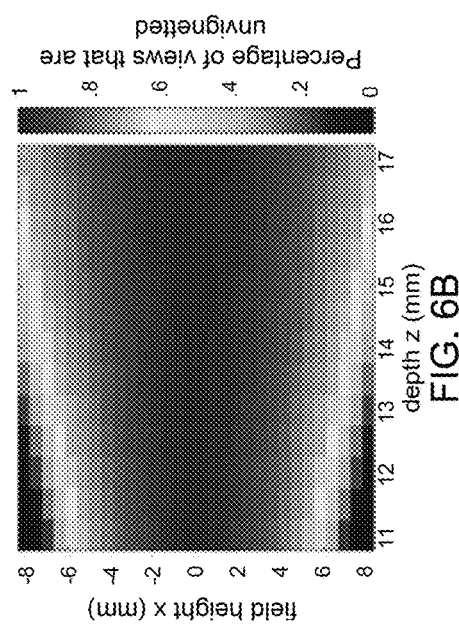
FIG. 6B is a pseudo-color chart showing vignetting as a function of field position and depth.

FIG. 6B shows the percentage of unvignetted rays for a point source located in the x-z (lateral-depth) plane in the object space. Due to rotational symmetry, the vignetting plot for a point source located in the y-z plane will be similar.

Figure 6D:
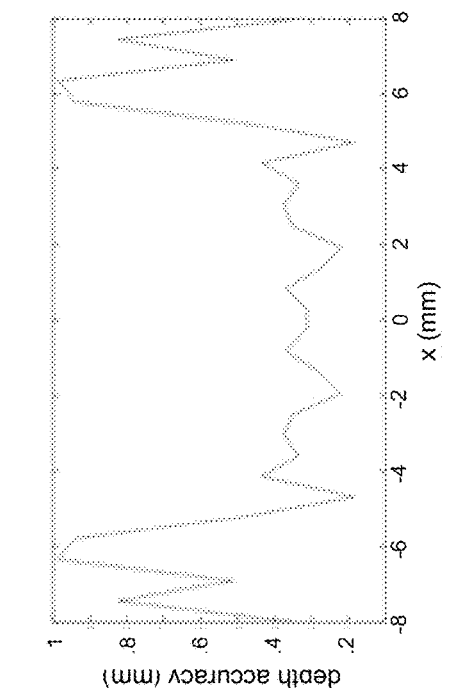
FIG. 6D is a graph illustrating accuracy of depth estimates based on FIG. 6C, as a function of field position.
Figure 6C:
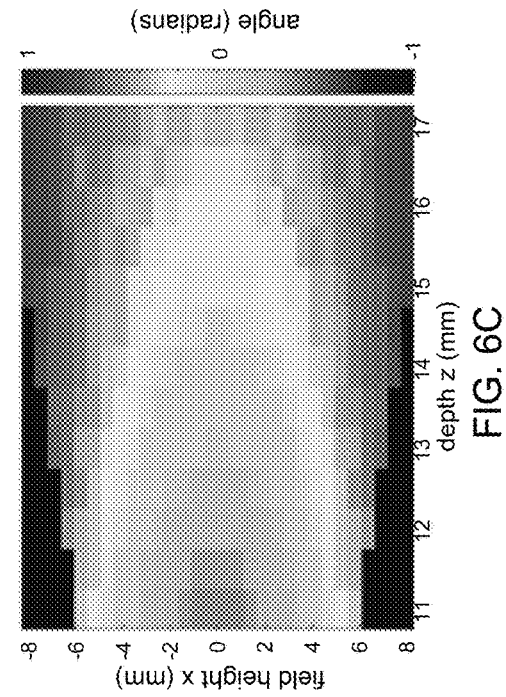
FIG. 6C is a pseudo-color chart showing a mapping of depth to angle, also as a function of field position.

Moreover, we also simulated the ray tracing through the entire plenoptic system and calculated the mapping between disparity angle and depth for a point source at different field heights. Light fields typically exhibit an inherent line structure in the (x,u) plane, where x is a space coordinate and u is a view coordinate. The disparity angle is the angle of the various lines in the line structure. Further details about disparity angle and this inherent line structure can be found in U.S. application Ser. No. 15/050,422, "Disparity-to-Depth Calibration for Plenoptic Imaging Systems," which is incorporated by reference herein. The disparity angle can be estimated based on the method described in U.S. application Ser. No. 14/064,090, "Processing of Light Fields by Transforming to Scale and Depth Space," which is incorporated by reference herein. FIG. 6C shows the resulting mapping of angle as a function of depth and field height x. Depth can be estimated by calculating the angle from the captured plenoptic images and then using the reverse mapping from angle to depth. One measure of the depth accuracy derived in this way is based on the standard deviation of a linear fitting between depths and angles. FIG. 6D plots this quantity as a function of different field heights x. The depth accuracy for the center region (distance from axis <5 mm) and peripheral region (distance from axis is 5-8 mm) are approximately 330 μm and 800 μm, respectively.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. For example, the specific lens prescription given in Table I is just an example. Even in that example, the lens surface parameters and thicknesses can be further optimized to decrease the aberrations, such as distortion and vignetting. Therefore, the scope of the invention should be determined by the appended claims and their legal equivalents.

What is claimed is:

1. A light field otoscope comprising:
an objective lens group for imaging an interior of a human ear, the objective lens group characterized by a pupil plane and an image plane;
a plenoptic sensor comprising a microlens array and a sensor array; and
relay optics positioned between the objective lens group and the plenoptic sensor, the relay optics relaying the image plane to the microlens array and relaying the pupil plane to the sensor array, wherein the relay optics comprises:
a first relay lens group that relays the pupil plane to an intermediate pupil plane; and
a second relay lens group that relays the intermediate pupil plane to the sensor array, the first and second relay lens groups together relaying the image plane to the microlens array, and wherein a filter module is insertable at the intermediate pupil plane.

2. The light field otoscope of claim 1 wherein the pupil plane is located ahead of a front lens of the objective lens group.

3. The light field otoscope of claim 1 wherein the objective lens group consists of a doublet followed by a singlet.

4. The light field otoscope of claim 1 wherein the objective lens group is specified substantially according to a lens prescription of:

| Surf | Type | Radius | Thickness | Glass | Conic |
|---|---|---|---|---|---|
| 1 | STANDARD | 5.33 | 1.00 | N-BK7 | −17.08 |
| 2 | STANDARD | −4 | 1 | N-5F5 | |
| 3 | STANDARD | −3.7 | 2 | | |
| 4 | STANDARD | 7 | 0.92 | N-BK7 | |
| 5 | STANDARD | −7 | 2.2. | | |

5. The light field otoscope of claim 1 wherein the objective lens group consists of a first positive lens group and a second positive lens group, the pupil plane located ahead of both lens groups.

6. The light field otoscope of claim 1 wherein the objective lens group has an object-space numerical aperture of at least 0.05.

7. The light field otoscope of claim 1 wherein the objective lens group has a field of view of at least 16 mm.

8. The light field otoscope of claim 1 wherein the objective lens group has an RMS spot size of not more than 6 microns on-axis.

9. The light field otoscope of claim 1 wherein chief rays in an image space of the objective lens group are telecentric or near-telecentric.

10. The light field otoscope of claim 1 wherein the objective lens group is specified substantially according to a lens prescription of:

| Surf | Type | Radius | Thickness | Glass |
|---|---|---|---|---|
| 1 | STANDARD | 5.38 | 1 | S-PHM52 |
| 2 | STANDARD | −5.38 | 1 | N-LASF9 |
| 3 | STANDARD | −20.79 | 1.2 | |
| 4 | STANDARD | 5.26 | 1.47 | N-BK7 |
| 5 | STANDARD | −3.98 | 1.03 | N-SF5 |
| 6 | STANDARD | −12.05 | 0.8 | |
| 7 | STANDARD | 7.12 | 2 | N-BAF10 |
| 8 | STANDARD | −4.22 | 1 | N-SF10 |
| 9 | STANDARD | −33.66. | | |

11. The light field otoscope of claim 1 wherein the objective lens group consists of a first negative lens group and a second positive lens group separated by the pupil plane.

12. The light field otoscope of claim 1 wherein the objective lens group is specified substantially according to a lens prescription of:

| Surf | Type | Radius | Thickness | Glass |
|---|---|---|---|---|
| 1 | STANDARD | −1.51 | 0.5 | N-BK7 |
| 2 | STANDARD | −1.66 | 0.5 | |
| 3 | STANDARD | Infinity | 0 | |
| 4 | STANDARD | 3.45 | 1.37 | N-BK7 |
| 5 | STANDARD | −1.38 | 0.83 | N-SF5 |
| 6 | STANDARD | −2.87 | 2 | |
| 7 | STANDARD | 10.14 | 1.68 | N-BK7 |
| 8 | STANDARD | −16.85 | 1 | N-SF5 |
| 9 | STANDARD | −10.65 | 0.7 | |

13. The light field otoscope of claim 1 wherein the objective lens group has an object-space numerical aperture of at least 0.03.

14. The light field otoscope of claim 1 wherein the objective lens group has a field of view of at least 30 degrees.

15. The light field otoscope of claim 1 wherein the objective lens group has an RMS spot size of not more than 30 microns.

16. The light field otoscope of claim 1 wherein the objective lens group has a magnification of between −0.1 and −1.0.

17. The light field otoscope of claim 1 wherein the objective lens group has vignetting of not more than 20% at focus plane.

18. The light field otoscope of claim 1 wherein the light field otoscope has an aperture of at least 3 mm in diameter.

19. The light field otoscope of claim 1 further comprising:
an inner housing containing the objective lens group, the inner housing shaped to be covered by a speculum.

20. A system for diagnosing conditions of the ear, comprising the light field otoscope of claim 1 and a computing system coupled to the light field otoscope, the light field otoscope capturing plenoptic images of an interior of the ear of a patient, the computing system processing the plenoptic images to assist in diagnosis of conditions of the ear.

* * * * *